(12) United States Patent
Otsuka

(10) Patent No.: US 6,638,063 B2
(45) Date of Patent: Oct. 28, 2003

(54) OPTICAL APPARATUS AND RESIN CURING APPARATUS

(75) Inventor: Masahiro Otsuka, Yokohama (JP)

(73) Assignee: Toei Electric Co., Ltd., Kanagawa (JP)

( * ) Notice: Subject to any disclaimer, the term of this patent is extended or adjusted under 35 U.S.C. 154(b) by 31 days.

(21) Appl. No.: 09/840,603

(22) Filed: Apr. 23, 2001

(65) Prior Publication Data
US 2001/0038992 A1 Nov. 8, 2001

(30) Foreign Application Priority Data

| May 2, 2000 | (JP) | 2000-133706 |
| May 10, 2000 | (JP) | 2000-137200 |

(51) Int. Cl.[7] ............................................. A61C 1/00
(52) U.S. Cl. ............................................. 433/29
(58) Field of Search .................... 433/29; 362/553, 362/555, 259, 340; 359/641

(56) References Cited

U.S. PATENT DOCUMENTS

| 3,666,180 A | * | 5/1972 | Cooms et al. ............... 433/29 |
| 4,337,759 A | * | 7/1982 | Popovich et al. | |
| 5,634,711 A | * | 6/1997 | Kennedy et al. ............... 433/29 |
| 5,680,256 A | * | 10/1997 | Katsuma ..................... 359/641 |
| 5,803,729 A | * | 9/1998 | Tsimerman .................. 433/29 |
| 6,102,696 A | * | 8/2000 | Osterwalder et al. ......... 433/29 |
| 6,200,134 B1 | * | 3/2001 | Kovac et al. ................. 433/29 |

FOREIGN PATENT DOCUMENTS

| JP | 7-240536 | 9/1995 | ........... H01L/33/00 |
| JP | 9-28719 | 2/1997 | ........... A61C/13/15 |
| JP | 2979522 | 9/1999 | ........... H01L/33/00 |

* cited by examiner

Primary Examiner—Todd E. Manahan
(74) Attorney, Agent, or Firm—Michael Best & Friedrich LLC (57) ABSTRACT

The present invention provides a resin curing apparatus which can cure light-cured resin in a small period of time after emitting a light ray for curing resin, and a small and light optical apparatus which can condense a parallel light ray incident upon an entrance plane in an area narrower than that at the time of incidence upon the entrance plane without attenuating optical intensity. The resin curing apparatus of the present invention includes a plurality of light emitting devices are caused to emit a light ray by a drive electric current larger than a rated electric current while forcibly cooling each light emitting device by a cooling fan, thereby obtaining a large quantity of light with the high optical intensity capable of curing resin in a short period of time.

10 Claims, 6 Drawing Sheets

OPTICAL APPARATUS AND RESIN CURING APPARATUS

CROSS-REFERENCE TO RELATED APPLICATIONS

This application is based upon and claims the benefit of priority from the prior Japanese Patent Applications No. 2000-133706, filed May 2, 2000; and No. 2000-137200, filed May 10, 2000, the entire contents of both of which are incorporated herein by reference.

BACKGROUND OF THE INVENTION

The present invention relates to an optical apparatus for condensing a parallel light ray incident upon an entrance plane in an area narrower than that when the parallel light ray reaches the entrance plane without attenuating optical intensity, and a resin curing apparatus for emitting a light ray having a predetermined wavelength for curing photo-cured resin, namely, light-cured resin toward a curing target by using this optical apparatus. More particularly, the present invention relates to a dental resin curing apparatus which is used in the oral cavity and capable of curing in a short period of time resin used for protecting a cut part in a mouth cavity and moisture proof.

As a dental resin curing apparatus, there is known one having a power supply device, LEDs, an optical fiber and a light irradiation head as disclosed in, for example, Japanese Patent Publication (Kokai) No. 4-30275.

The resin curing apparatus (resin curing light source apparatus) disclosed in the above-mentioned patent application uses a plurality of LEDs which emit a light ray having a wavelength of 455 nm for a light source, and supplies the light ray to the light irradiation head through the optical fiber so that a predetermined position in a mouth cavity (irradiation target) is irradiated with the light ray from the light irradiation head.

Incidentally, according to the above-mentioned patent application, there is the description that the LED as the light source has approximately 20 LED chips with the optical output of 1200 $\mu$W being arranged therein.

Further, Japanese Patent Publication (Kokai) No. 9-28719 discloses a polymerization apparatus which uses a battery as a power supply and has a solid radiant ray emitter and an optical transmission path being integrated with each other so that the apparatus can be easily used.

In the resin curing apparatus, the wavelength of a light ray emitted by the LED chip is 430 to 480 nm and blue because of the curing characteristic of resin. However, as generally known, the optical output of the LED emitting a blue light ray is a fraction of that of, e.g., a red light ray (wavelength: 680 nm) or an orange light ray (wavelength: 580 nm) to this day, and it requires several tens seconds to completely cure the light-cured resin situated at a predetermined position in the oral cavity.

Therefore, there is a problem that an uncomfortable posture is demanded for a relatively long time to a patient who comes for a treatment in his/her oral cavity and a treatment for a decayed tooth in particular so that he/she does not close his/her mouth.

Furthermore, there is a problem that a specific posture for light emission is demanded to a doctor who is going to cure the resin in such a manner that the doctor maintains the same posture to emit the light ray having a predetermined wavelength so that a part at which the resin is used is continuously irradiated with the light ray until the resin is cured.

This makes the labor conditions (posture for treatment) for doctors severe and increases recognition by patients that the treatment time is long the dental treatment is painful.

Moreover, when a plurality of light emitting devices are used to increase the optical intensity, a light ray or a parallel light ray from each light emitting device must be condensed into a dimension so that the light can be inserted into or approximate the oral cavity. However, a technique for condensing the light or the parallel light ray from each light emitting device in an area narrower than that at the time of incidence upon an entrance plane without attenuating the optical intensity is not currently established.

Thus, both the condenser and the resin curing apparatus become large in size and weight, and they are not necessarily easy to be used for doctors. In addition, heat generation from the light emitting device causes both a patient and a doctor to feel thicknesses of these apparatuses.

BRIEF SUMMARY OF THE INVENTION

It is an object of the present invention to provide a resin curing apparatus capable of curing light-cured resin in a small time after irradiation of a light ray for curing the resin.

Additionally, it is another object of the present invention to provide an optical apparatus capable of condensing a parallel light ray incident upon an entrance plane in an area narrower than that at the time of incidence upon the entrance plane without attenuating optical intensity.

According to the present invention is to provide a resin curing apparatus comprising:

a light source having a plurality of light emitting devices for emitting a light rays each having a predetermined wavelength;

a condenser having a first surface on which the respective light emitting devices of the light source are closely or proximally arranged, a second surface which has a light outgoing radiation area narrower than the first surface and causes a light ray incident upon the first surface to outgo in a predetermined direction, and a dioptric member which includes a material which is filled between the first surface and the second surface, optically transparent with respect to a wavelength of a light ray emitted by each of the light emitting devices and condenses a light ray from each of the light emitting devices of the light source in an area narrower than that at the time of incidence upon the first surface to be led to the second surface; and a guide member for guiding a light ray condensed by the condenser to a predetermined position.

According to the present invention is to provide a resin curing apparatus comprising:

a light source having a plurality of light emitting devices, the respective light emitting devices being arranged in such a manner that traveling directions of light rays emitted by the respective light emitting devices become the same direction, and each of the light emitting device emitting a light ray having a predetermined wavelength;

a condenser having a first curved surface on which the respective light emitting devices of the light source are closely or proximally arranged, a second curved surface which has a light outgoing radiation area narrower than the first curved surface and causes a light ray incident upon the first curved surface to outgo in a predetermined direction, and a dioptric member which includes a material which is filled between the first curved surface and the second curved surface, optically transparent with respect to a wavelength of a light ray emitted by each of the light emitting devices and condenses a light ray from each of the light emitting devices of the light source in an area narrower than that at the time of incidence upon the first curved surface to be led to the second curved surface; and a guide member for guiding a light ray condensed by the condenser to a predetermined position.

According to the present invention is to provide a resin curing apparatus comprising:

a light source which is an LED array including a plurality of LEDs each of which outputs a light ray having a predetermined wavelength, the respective LEDs being arranged in the LED array in such a manner that traveling directions of light rays emitted by the respective LEDs become the same direction;

a guide member for guiding a light ray from the light source to a predetermined position; and a cooling fan for forcibly cooling the LED array and a drive motor of the cooling fan itself.

According to the present invention is to provided an optical apparatus comprising:

a first curved surface on which a light ray from a light source including a number of light emitting devices can be incident, the shape of the first curved surface being defined in such a manner that at least one of the light emitting devices in close contact with each other and the light emitting devices arranged in contiguity with each other can be aligned along the first curved surface;

a second curved surface which has a light outgoing radiation area narrower than the first curved surface and causes a light ray incident upon the first curved surface to outgo in a predetermined direction; and an optically transparent material which is filled between the first curved surface and the second curved surface, optically transparent with respect to a wavelength of a light ray emitted by each of the light emitting devices, and condenses the light ray from each of the light emitting devices of the light source to an area narrower than that at the time of incidence upon the first curved surface to be led to the second curved surface.

According to the present invention is to provide an optical apparatus comprising:

a first curved surface having a predetermined curvature by which a parallel ray can be incident upon the first curved surface;

a second curved surface which has a light outgoing radiation area narrower than the first curved surface and causes a light ray incident upon the first curved surface to outgo in a predetermined direction; and an optically transparent material which is filled between the first curved surface and the second curved surface, optically transparent with respect to a wavelength of the parallel ray, and condenses the parallel ray in an area narrower than that at the time of incidence upon the first curved surface to be led to the second curved surface.

Additional objects and advantages of the invention will be set forth in the description which follows, and in part will be obvious from the description, or may be learned by practice of the invention. The objects and advantages of the invention may be realized and obtained by means of the instrumentalities and combinations particularly pointed out hereinafter.

BRIEF DESCRIPTION OF THE SEVERAL VIEWS OF THE DRAWING

The accompanying drawings, which are incorporated in and constitute a part of the specification, illustrate presently preferred embodiments of the invention, and together with the general description given above and the detailed description of the preferred embodiments given below, serve to explain the principles of the invention.

DETAILED DESCRIPTION OF THE INVENTION

A preferred embodiment according to the present invention will now be described in detail hereinafter with reference to the accompanying drawings.

Figure 1:
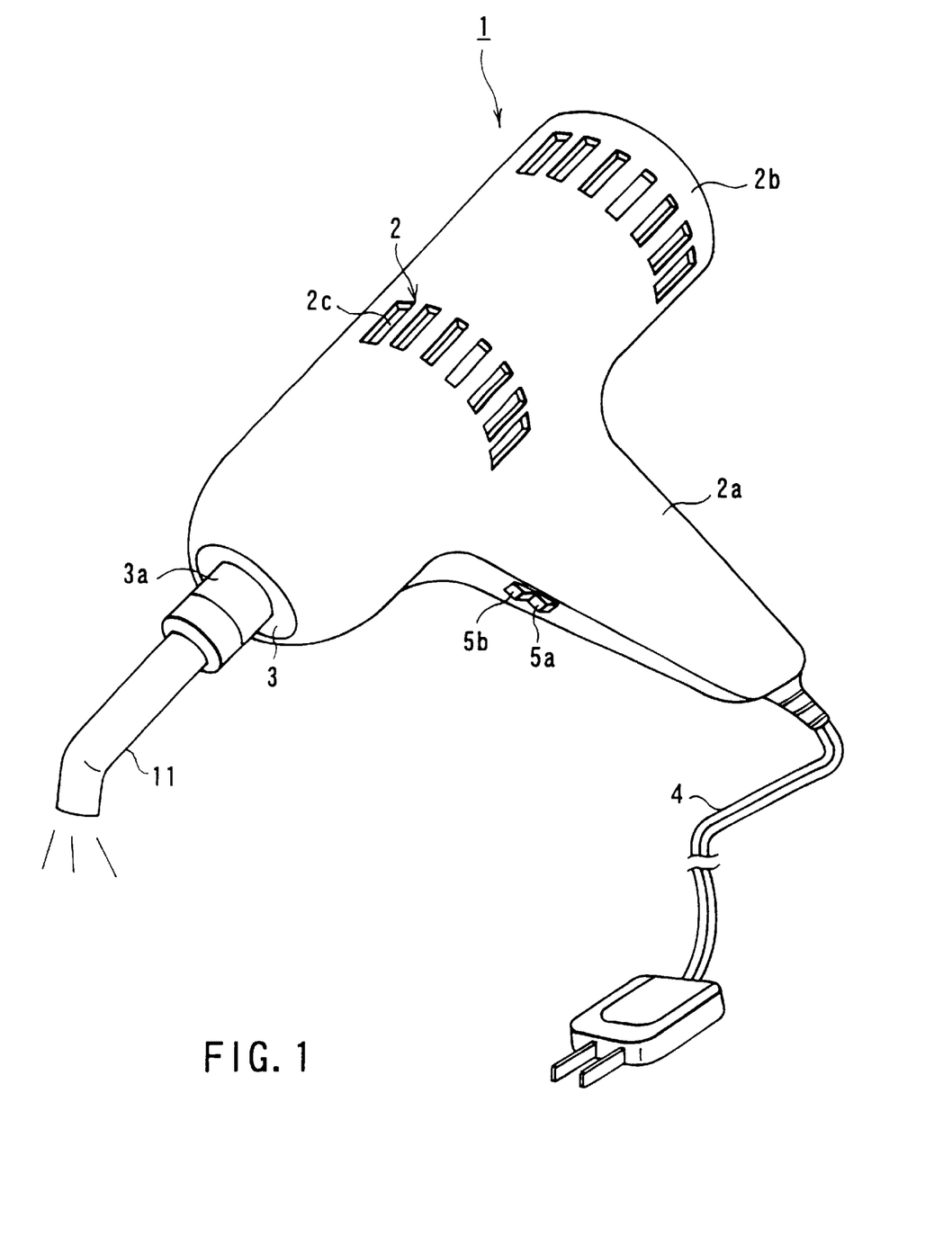
FIG. 1 is a schematic view for illustrating a resin curing apparatus according to the present invention.

FIG. 1 is a schematic view for illustrating a resin curing apparatus according to the present invention.

As shown in FIG. 1, the resin curing apparatus 1 is constituted by an apparatus main body 2, a light guide connection portion 3 provided at an end of the apparatus main body 2, and a power supply line 4 connected to the apparatus main body 2 through a grip portion 2a of the apparatus main body 2. It is to be noted that the light guide connection portion 3 includes a coupler 3a, and a light guide (optical fiber assembly in which optical fibers are assembled in a predetermined shape) 11 having an opening cross-sectional shape is detachably formed. As a result, the light guides 11 having different dimensions can be arbitrarily replaced in accordance with uses or ages of patients.

Further, as will be described later with reference to FIG. 2, a power supply which takes out a predetermined voltage and electric current from a commercial power source supplied through the power supply line 4 is accommodated inside the grip portion 2a of the apparatus main body 2. It is to be noted that a pair of switches 5a (for the main power supply) and 5b (for LED light emission) for energizing the power supply and turning on/off the light source are provided at arbitrary positions of the grip portion 2a. Incidentally, the pair of switches 5a and 5b may be a pair of cooperative switches and may have a time limit function that one is turned on when the other is turned on and one of them is shut off after elapse of a predetermined time.

Figure 2:
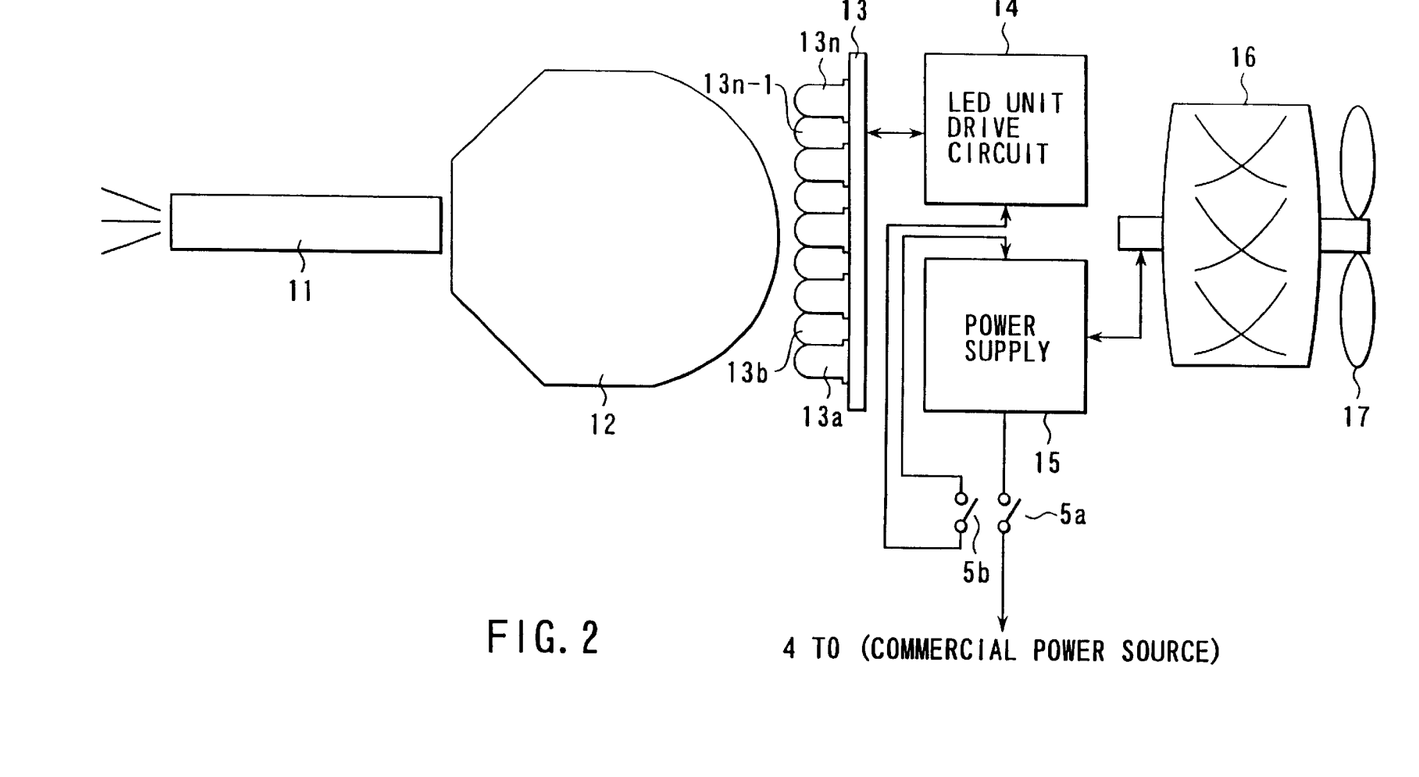
FIG. 2 is a schematic view for illustrating an internal structure of the resin curing apparatus shown in FIG. 1.

As shown in FIG. 2, in the vicinity of one end of the light guide 11, there is provided a condenser 12 which condenses the light emitted by respective LEDs 13a, . . . , 13n in an LED array 13 in an area having a diameter smaller than that defined by the respective LEDs 13a, . . . , 13n with a predetermined gap or in close contact with the light guide 11.

To each of the LEDs 13a, . . . , 13n of the LED array 13 is connected an LED drive unit circuit 14 which has a predetermined voltage transformed by the power supply 15 and to which a predetermined LED drive electric current can be supplied. When the switches 5a and 5b are turned on, an electric current with a predetermined intensity is supplied to the LED drive unit circuit 14 with a predetermined voltage.

It is to be noted that the power supply 15 and the LED drive unit circuit 14 are formed into predetermined shapes so that they can be accommodated in the grip portion 2a of the apparatus main body 2 shown in FIG. 1 for example, and they supply an appropriate load to the grip portion 2a so that the apparatus main body 2 can be easily used. Further, as will be described later with reference to FIG. 5, when one of the switches 5a and 5b is turned on (5a in this example), the remaining switch (5b in this example) is simultaneously turned on. Since the switch 5b connected to the LED drive unit circuit 14 side is connected to a timer (time limit function) 14a which is shut off after elapse of a predetermined time, energization to at least the LED drive unit circuit 14 side can be interrupted when a predetermined time, for example, five seconds pass after.

To the power supply 15 are connected a direct-current drive type or alternating-current drive type fan motor 16 and a cooling fan 17 integrally formed with the fan motor 16. This fan 17 is accommodated on the side of an exhaust port 2b which is on the side apart from the fiber connection portion 3 of the apparatus main body 2 shown in FIG. 1 for example. When the fan motor 16 is rotated, the fan 17 sucks an air flow for cooling from an intake port 2c provided at a substantially central portion of the apparatus main body 2 in the longitudinal direction and cools down the respective LEDs 13a, . . . , 13n in the LED array 13 and the motor 16 to generate the air flow for cooling which goes through the exhaust port. The operation of the respective LEDs 13a, . . . , 13n is stabilized, and increase in a temperature prevents the optical characteristic of the condenser 12 from fluctuating.

Figure 3A:
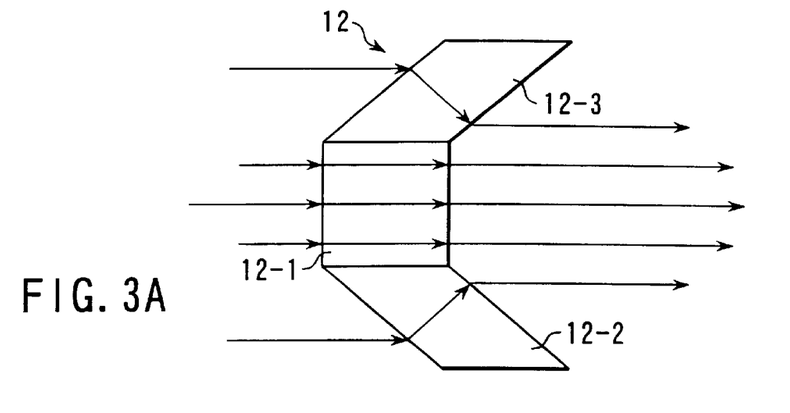
FIG. 3A is a schematic diagram illustrating the principle of a condenser which converts a light ray emitted from each LED in an LED array into an area narrower than that at the time of incidence and increases the optical intensity for outgoing radiation in the resin curing apparatus shown in FIGS. 1 and 2.

FIG. 3A is a schematic view for illustrating the principle of the condenser which converts the light emitted from each LED in the LED array in the resin curing apparatus shown in FIGS. 1 and 2 into an area narrower than that at the time of incidence and increases the optical intensity for outgoing radiation.

As shown in FIG. 3A, the light incident upon a part 12-1 at which an entrance plane is orthogonal to the incident light (indicated by an arrow) outgoes from the condenser 12 in which a plurality of parallel flat plates are connected with each other as it stands.

On the other hand, the light incident upon each of parts 12-2 and 12-3 at which each of the entrance plane is formed into a parallelogram so that the entrance plane has a predetermined angle with respect to the incident light is bent at a predetermined angle at each of the parallelogram part 12-2 and 12-3 by the law of refraction. Further, when the light outgoes from each of the parallelogram part 12-2 and 12-3, it is returned to be parallel with the incident right.

As a result, the light outgoing from the condenser 12 is condensed in an area narrower than a cross section area at the time of incidence. Furthermore, the optical intensity is increased to be higher than that at the time of incidence even if losses due to the condenser are excluded.

It is to be noted that the degree of condensing by the condenser 12 can be arbitrarily set in accordance with a material and a thickness of the condenser 12.

Figure 3B:
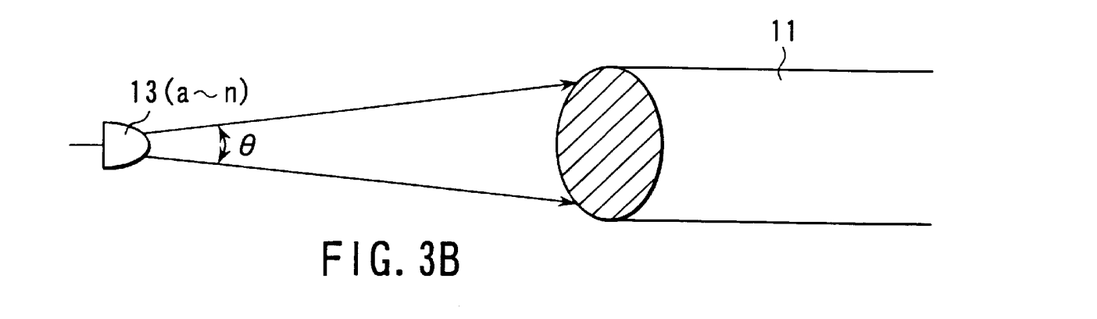
FIG. 3B is a schematic diagram depicting the conditions in which the light emitted from each LED of the LED array is applied to a light guide.

FIG. 3B illustrates the conditions in which the light emitted from each LED 13a of the LED array is applied to the light guide 11. Since the light emitted from each LED 13a diverges as shown in FIG. 3B, it cannot be applied in its entirety to the light guide 11 if the LED 13a is spaced far from the light guide 11. Further, the light cannot pass through the light guide 11 unless it is applied to the guide 11 at an angle θ of incidence that falls within a specific range since the light beams from the other LEDs 13a must pass through the guide 11, too. Nonetheless, the light beams emitted from all LEDs 13a are successfully applied to the light guide 11. This is because the condenser 12 converges the light beams at a small region, thus guiding more beams to the light guide 11 than an ordinary light-converging plate.

Figure 4A:
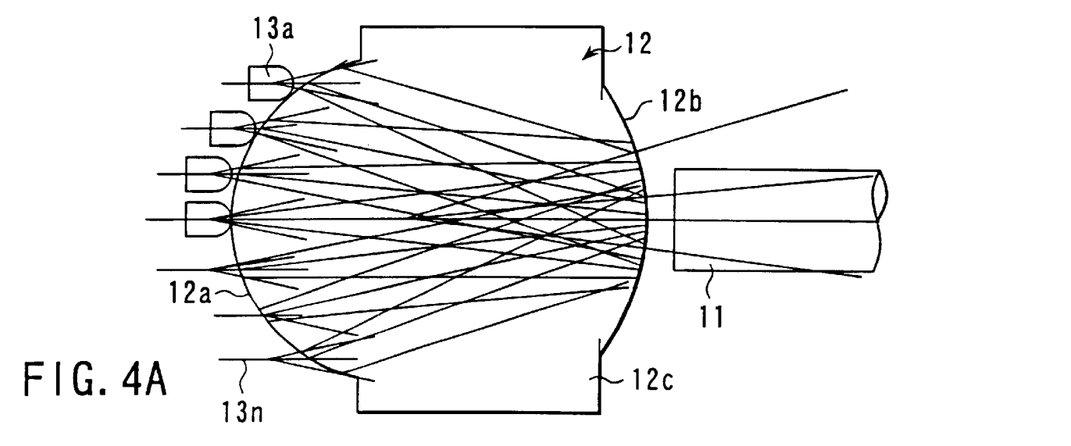
FIGS. 4A and 4B are schematic views for illustrating a condenser applied to the resin curing apparatus shown in FIGS. 1 and 2.

FIG. 4A is a schematic view for illustrating the condenser applied to the resin curing apparatus shown in FIGS. 1 and 2.

As shown in FIG. 4A, the condenser 12 is constituted by a first curved surface (entrance plane) 12a on which respective LEDs 13a, . . . , 13n in the LED array 13 are arranged in close contact with each other or at predetermined intervals, a second curved surface (outgoing radiation plane) 12b from which the light incoming from the first curved surface 12a outgoes, and a condensing member (main body) 12c which is transparent with respect to a wavelength of the light emitted by each of the LEDs 13a, . . . , 13n. The condenser 12 changes the optical path of the light incident upon the first curved surface 12a by the main body 12c and condenses the light on the second curved surface 12b narrower than the first curved surface 12a. It is to be noted that the condensing member (main body) 12c is formed of, e.g., optical glass, quartz glass or acryl.

Moreover, as shown in the drawing, when the respective LEDs 13a, . . . , 13n in the LED array 13 are arranged along the first curved surface 12a in such a manner that the light rays emitted by the LEDs 13a, . . . , 13n have substantially the same direction, the first curved surface 12a is given a predetermined curvature such that most of the light rays from the respective LEDs 13a, . . . . 13n are refracted toward the central side of the main body 12c.

On the other hand, as shown in the drawing, the second curved surface 12b is given a curvature for enabling the second curved surface 12b to function as a condenser lens (convex lens) for causing the light which has passed through the main body 12c to be efficiently incident upon the light guide 11 (coupling the light which has passed through the condenser 12 with the light guide 11).

It is to be noted that on the first curved surface 12a are formed a non-illustrated reflection preventing film (reflection preventing coating) for suppressing reflection of the light from the respective LEDs 13a, . . . , 13n on the first curved surface 12a to return to the outside of the condenser 12 and a similar reflection preventing film (reflection preventing coating) for suppressing reflection of the light which has passed through the main body 12c on the second curved surface 12b to return to the main body 12c, respectively.

According to this condenser 12, the parallel light ray incident upon the entrance plane (first curved surface 12a) can be condensed in an outgoing radiation plane (second curved surface 12b) narrower than that at the time of incidence upon the entrance plane 12a without attenuating the optical intensity.

Figure 4B:
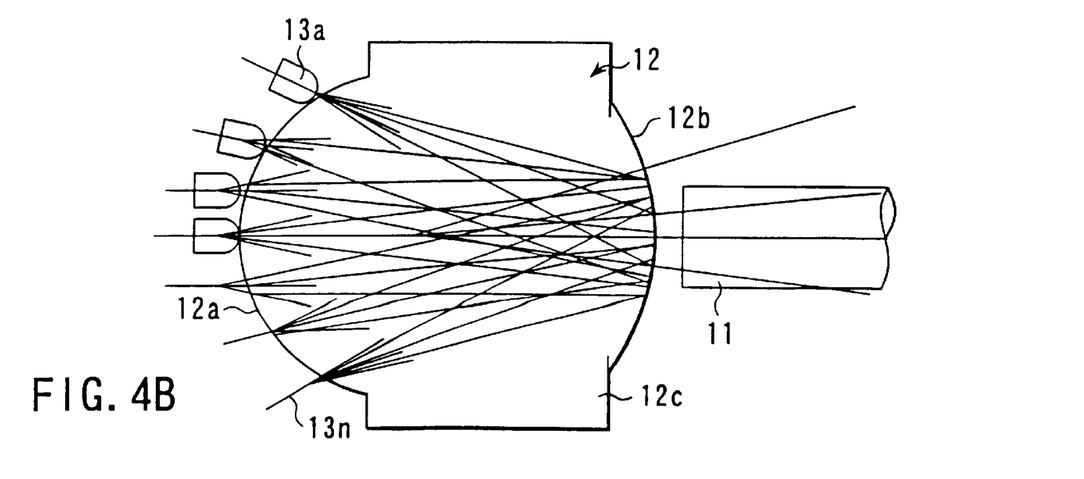

FIG. 4B is a schematic view for illustrating the condenser shown in FIG. 4A.

As shown in FIG. 4B, the condenser 12 changes the optical path of the light incident upon the first curved surface 12a by the main body 12c and condenses the light on the second curved surface 12b narrower than the first curved surface 12a. It is to be noted that the condensing member (main body) 12c is formed of, e.g., optical glass, quartz glass or acryl.

Moreover, as shown in the drawing, when the respective LEDs 13a, . . . , 13n in the LED array 13 are arranged along the first curved surface 12a in such a manner that the light rays emitted by the LEDs 13a, . . . , 13n have radially and directed to a center of the second curved surface 12b.

On the other hand, as shown in the drawing, the second curved surface 12b is given a curvature for enabling the second curved surface 12b to function as a condenser lens (convex lens) for causing the light which has passed through the main body 12c to be efficiently incident upon the light guide 11 (coupling the light which has passed through the condenser 12 with the light guide 11).

Need less to say, on the first curved surface 12a are formed a non-illustrated reflection preventing film for suppressing reflection of the light from the respective LEDs 13a, . . . , 13n on the first curved surface 12a to return to the outside of the condenser 12 and a similar reflection preventing film for suppressing reflection of the light which has passed through the main body 12c on the second curved surface 12b to return to the main body 12c, respectively.

According to this condenser 12, the radially directed light ray incident upon the entrance plane (first curved surface 12a) can be condensed in an outgoing radiation plane (second curved surface 12b) narrower than that at the time of incidence upon the entrance plane 12a without attenuating the optical intensity.

As a result, the dimension and the weight of the condenser 12 can be reduced, which improves the operability of treatment (freedom of treatment) by doctors.

Moreover, since the optical intensity of the condensed light is less attenuated, a number of LEDs required for the light source is reduced, thereby decreasing the power consumption and the calorific power. This is also advantageous to reduction in dimension and weight of the condenser 12.

Figure 5:
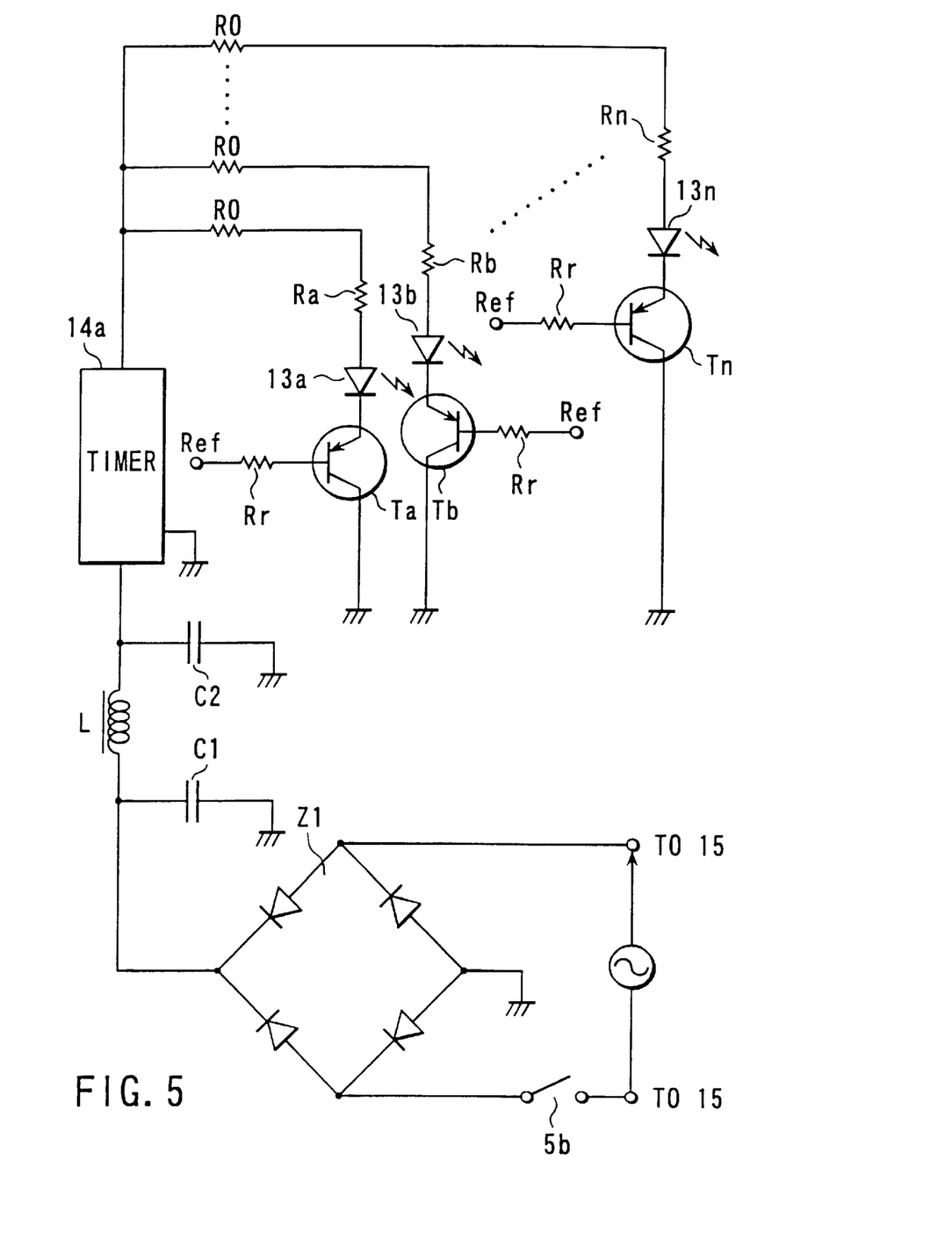
FIG. 5 is a schematic block diagram showing an example of an LED drive circuit for causing each LED in the LED array to emit a light ray with a drive electric current larger than a rated current in the resin curing apparatus shown in FIGS. 1 and 2.

FIG. 5 is a schematic block diagram for illustrating an example of an LED drive unit 14.

An alternating-current voltage transformed into a predetermined voltage by the power supply circuit 15 is rectified by a bridge Z1, and the ripple is reduced by a smoothing portion consisting of L0, C1 and C2. The resulting voltage is inputted to a timer circuit 14a.

The direct-current voltage which has passed through the timer 14a is supplied to each of LEDs 13a to 13n through a protection resistance R0 and electric current limit resistances Ra to Rn allocated to each of the LEDs 13a to 13n. It is to be noted that the drive electric current supplied to each LED is controlled at an electric current value which is twofold to threefold of a rated electric current of each LED. At this time, the intensity of the drive electric current flowing through each LED is defined as 50 to 70 mA in case of the LED having the rated electric current of 20 mA, for example.

The switch 5b controls the light emitting time of the respective LEDs 13a to 13n in the LED array 13. When the switch 5a is turned on, the switch 5b supplies the direct-current voltage rectified by the bridge Z1 to the LED drive unit 14. Incidentally, the timer circuit 14a is a switching circuit which limits the energizing time for the respective LEDs 13a to 13n to a predetermined time, for example, five seconds and protects each LED which is emitting the light with the high brightness by a drive electric current larger than the rated electric current. The timer circuit 14a may be, for example, a logic circuit for turning on/off the gate voltage (Ref) of transistors Ta to Tn connected to the respective LEDs or a simple time limit switch.

When the switch 5a is turned on, energization to the power supply circuit 15 shown in FIG. 2 is assured independently from the operation of the timer circuit 14a, and the cooling fan 16 is rotated. Consequently, the LEDs 13a to 13n which are emitting the light with the high brightness are forcibly cooled down by the drive electric current larger than the rated electric current.

Figure 6:
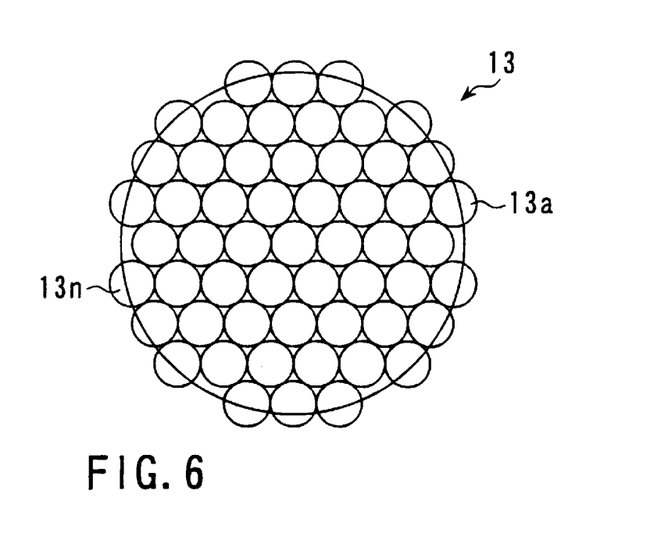
FIG. 6 is a schematic view for illustrating arrangement of LEDs in the LED array used as a light source in the resin curing apparatus shown in FIGS. 1 and 2.

FIG. 6 is a schematic view for illustrating arrangement of the LEDs in the LED array used as a light source in the resin curing apparatus shown in FIGS. 1 and 2.

As shown in FIG. 6, the respective LEDs 13a, . . . , 13n in the LED array 13 are arranged by the closest packing in such a manner that a largest part of the cylindrical or tapered outer peripheral portion of each LED is brought into contact with the counterpart so that line segments connecting the centers of the respective LEDs 13a, . . . , 13n form a substantial triangle (usually, a equilateral triangle).

Further, an area in which the respective LEDs 13a, . . . , 13n are arranged is defined as, for example, substantially a circle. Incidentally, assuming that a diameter of each of the LEDs 13a, . . . , 13n is, for example, 3 mm, the size (diameter) of the LED array 13 calculated from all the LEDs becomes approximately 25 mm.

It is to be noted that the wavelength of the light emitted by each of the LEDs 13a to 13n is, for example, 350 nm to 480 nm, and the LED emitting the light having the wavelength of 370 nm, 430 nm or 450 nm can be easily obtained in particular.

As a result, it is possible to provide the LED array 13 having the output optical intensity being a large output capable of condensing the light by the condenser 12 and curing a predetermined amount of light-cured resin put into, e.g., a mouth cavity in several seconds, for example, five seconds.

Figure 7:
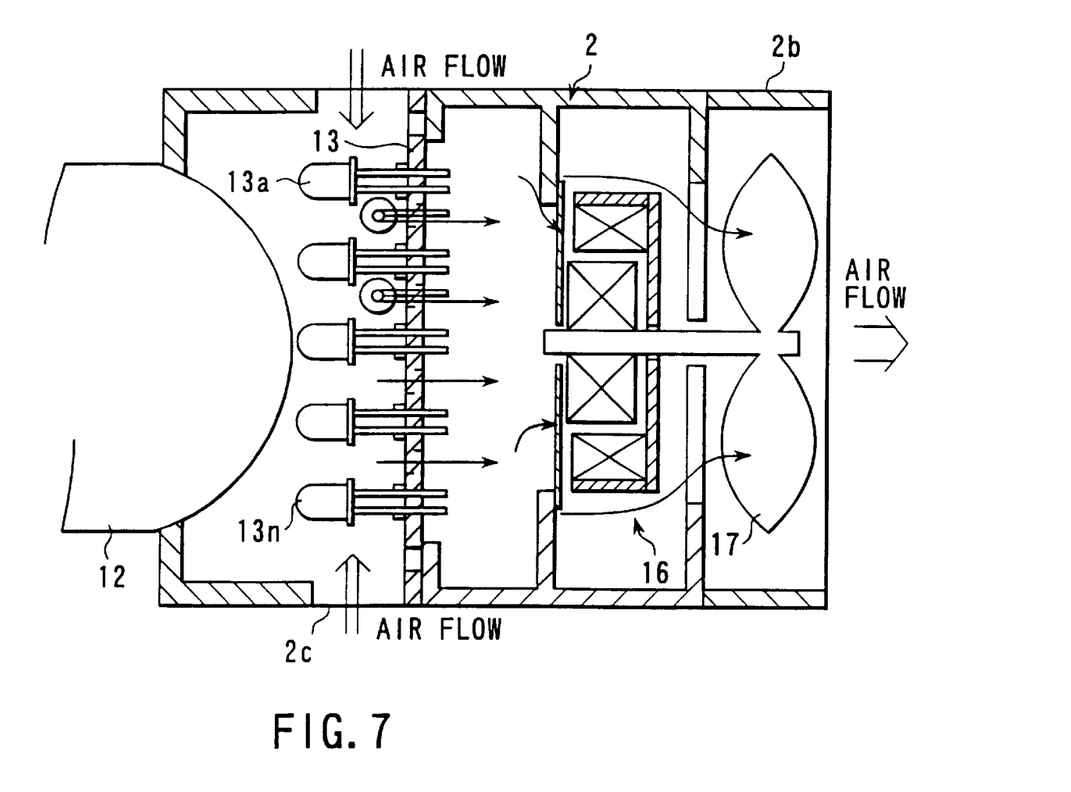
FIG. 7 is a schematic view for illustrating an air flow for cooling in the resin curing apparatus shown in FIGS. 1 and 2.

FIG. 7 is a schematic view for illustrating an air flow for cooling in a resin curing apparatus shown in FIGS. 1 and 2.

As shown in FIG. 7, when the fan motor 16 accommodated on the side of the exhaust port 2b on the side apart from the fiber connection portion 3 of the apparatus main body 2, e.g., the apparatus main body 2 depicted in FIG. 1 is rotated, the cooling blast taken from the intake port 2c provided at substantially the central portion of the apparatus main body 2 in the longitudinal direction is sucked by the cooling fan 17 while cooling down the respective LEDs 13a, . . . , 13n in the LED array 13 and the motor 16 and becomes the air flow for cooling which passes through the exhaust port 2b. Consequently, even if the LED array 13 generates heat more than usual by supply of the drive electric current higher than the rated electric current, the apparatus main body 2 or the LED array 13 is not undesirably heated, thereby enabling the stable light emitting operation. Furthermore, increase in a temperature can prevent the optical characteristic of the condenser from fluctuating.

Incidentally, since the dimension and the weight of the condenser 12 are small and attenuation of the optical intensity of the condensed light is small, a number of LEDs required for the light source is reduced. As a result, the calorific power is reduced, and the dimension and the weight of the cooling fan 17 can be also decreased.

Figure 8:
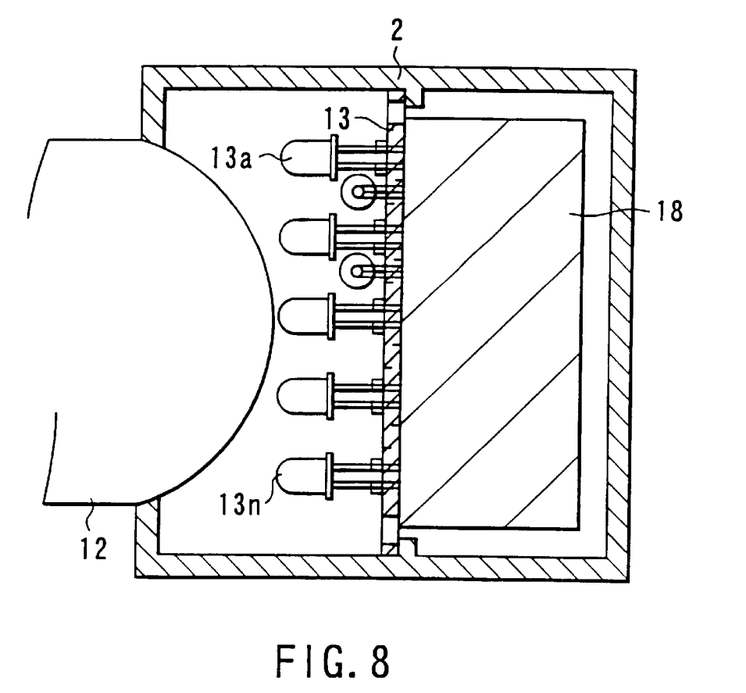
FIG. 8 is a diagram illustrating a cooling unit that may be used in place of the cooling unit shown in FIG. 7.

FIG. 8 shows a cooling unit 18 that may replace the cooling unit shown in FIG. 7, which includes the cooling fans 16 and 17. As shown in FIG. 8, the cooling unit 18 has a metal plate or a heat pipe that has high specific heat. The cooling unit of FIG. 8 may be secured to the back of the substrate of the LED array 13, to accumulate heat temporarily and then accomplish natural cooling. The cooling unit 18 can be made of Cu, Al, Ag, Au, brass, Fe, or the like.

As described above, in the resin curing apparatus according to the present invention, a plurality of light emitting devices are arranged in such a manner that the traveling directions of the light rays emitted by the respective light emitting devices become the same direction, and the condenser has the first curved surface on which the respective light emitting devices are closely or proximally arranged and the second curved surface which has a light outgoing radiation area narrower than the first curved surface and causes the light incident upon the first curved surface to outgo in a predetermined direction, the condenser consisting of the dioptric member having a material which is optically transparent with respect to a wavelength of the light emitted by each light emitting device being filled between the first curved surface and the second curved surface. Since the condenser condenses the light emitted from each light emitting device in an area narrower than that at the time of incidence upon the first curved surface and leads the light from the second curved surface to the light guide, it is possible to provide the resin curing apparatus which has the high optical intensity and can cure the dental resin in several seconds. Moreover, since a plurality of light emitting devices are driven by the drive electric current larger than the rated electric current and forcibly cooled down by the cooling fan, a large quantity of light can be obtained in a short period of time, thereby providing the resin curing apparatus which has the high optical intensity and can cure the dental resin in several seconds.

In addition, it is possible to provide the optical apparatus which condenses the parallel light ray incident upon the entrance plane in the area narrower than that at the time of incidence without attenuating the optical intensity. Consequently, the light source which is a factor of heat generation is reduced in size and capacity.

Incidentally, it is possible to reduce the time in which a patient who comes for a treatment in a mouth cavity, e.g., a treatment for a decayed tooth is asked for an uncomfortable posture so as not to close his/her mouth for a relatively long time. Additionally, it is possible to shorten the time in which a doctor who is in charge of a treatment in a mouth cavity must take a specific light irradiation posture in such a manner that a part at which the resin is placed is continuously irradiated with the light.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. A resin curing apparatus comprising:

a light source having a plurality of light emitting devices for emitting individually associated light rays, each of said light rays having a predetermined wavelength;

a condenser having a first surface on which said respective light emitting devices of said light source are closely or proximally arranged, a second surface which has an outgoing light radiation area that is narrower than said first surface, said second surface causing a light ray incident upon said first surface to exit in a predetermined direction, and a dioptric member which includes a material which is filled between said first surface and said second surface, said member being optically transparent with respect to said wavelength of a light ray emitted by each of said light emitting devices and condensing said light rays from each of said light emitting devices of said light source into an area that is narrower than said first curved area at the time of said incidence upon said first surface, said dioptric member leading said condensed light rays to exit said second surface; and a guide member for guiding said light rays condensed by said condenser to a predetermined position, said condensed light rays being parallel when exiting from said second surface.

2. A resin curing apparatus comprising:

a light source having a plurality of light emitting devices, said respective light emitting devices being arranged in such a manner that traveling directions of light rays emitted by said respective light emitting devices become the same direction, and each of said light emitting device emitting a light ray having a predetermined wavelength;

a condenser having a first curved surface on which said respective light emitting devices of said light source are closely or proximally arranged, a second curved surface which has a light outgoing radiation area narrower than said first curved surface and causes a light ray incident upon said first curved surface to outgo in a predetermined direction, and a dioptric member which includes a material which is filled between said first curved surface and said second curved surface, optically transparent with respect to a wavelength of a light ray emitted by each of said light emitting devices and condenses a light ray from each of said light emitting devices of said light source in an area narrower than that at the time of incidence upon said first curved surface to be led to said second curved surface; and a guide member for guiding a light ray condensed by said condenser to a predetermined position.

3. The resin curing apparatus according to claim 2, wherein said light source, said condenser and said guide member are integrally formed.

4. The resin curing apparatus according to claim 3, wherein each of said light emitting devices of said light source is an LED which emits a light ray having a wavelength of 430 to 480 nm and said light source is an LED array in which a plurality of said LEDs are arranged.

5. The resin curing apparatus according to claim 3, wherein said first curved surface of said condenser directs a light ray emitted by each of said light emitting devices of said light source to a curvature center side of said first curved surface.

6. The resin curing apparatus according to claim 3, wherein a power supply device for driving said light source is further integrally incorporated.

7. The resin curing apparatus according to claim 2, wherein each of said light emitting devices of said light source is an LED which emits a light ray having a wavelength of 430 to 480 nm and said light source is an LED array in which a plurality of said LEDs are arranged.

8. The resin curing apparatus according to claim 7, wherein a power supply device for driving said light source is further integrally incorporated.

9. The resin curing apparatus according to claim 2, wherein said first curved surface of said condenser directs a light ray emitted by each of said light emitting devices of said light source to a curvature center side of said first curved surface.

10. The resin curing apparatus according to claim 9, wherein a power supply device for driving said light source is further integrally incorporated.

* * * * *